US00PP33052P2

(12) United States Plant Patent
Ammerlaan

(10) Patent No.: US PP33,052 P2
(45) Date of Patent: May 11, 2021

(54) ***ECHEVERIA* PLANT NAMED 'OVPEARLS07'**

(50) Latin Name: ***Echeveria agavoides* x *Echeveria elegans* var. *simulans***
Varietal Denomination: OVPEARLS07

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/899,850

(22) Filed: Jun. 12, 2020

(30) Foreign Application Priority Data

Nov. 27, 2019 (QZ) ..... PBR 2019/3115

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32
See application file for complete search history.

*Primary Examiner* — Anne Marie Grunberg
(74) *Attorney, Agent, or Firm* — Samuel R. McCoy, Jr.

(57) ABSTRACT

A new and distinct variety of *Echeveria* plant named 'OVPEARLS07' which is characterized by a globular prolife with an abundance of foliage that is tightly held in a basal rosette, greyed-green foliage that is lightly to moderately covered with light greyed-green epicuticular wax, and dark red leaf margins at and near the apex. The new variety has shown to be uniform and stable in the resulting generations from asexual propagation.

4 Drawing Sheets

Latin name of the genus and species: The Latin name of the genus and species of the novel variety disclosed herein is *Echeveria agavoides* x *Echeveria elegans* var. *simulans.*

Variety denomination: The inventive variety of *Echeveria* disclosed herein has been given the variety denomination 'OVPEARLS07'.

CROSS REFERENCE TO RELATED APPLICATIONS

This application claims priority to the Community Plant Variety Rights application number 2019/3115, filed on Nov. 27, 2019, which is herein incorporated by reference.

BACKGROUND OF THE INVENTION

Parentage: 'OVPEARLS07' is a seedling selection resulting from the controlled pollination of an unnamed *Echeveria agavoides* plant (unpatented), the seed parent, with an unnamed *Echeveria elegans* var. *simulans* plant (unpatented), the pollen parent. The crossing was made by the inventor in November of 2008 at a commercial greenhouse in Bleiswijk, the Netherlands. In March of 2009, one seedling was observed which exhibited unique foliage and growth characteristics when compared to the parent plants and all other progeny. After confirming the stability of the unique characteristics first observed, the new plant was selected for commercialization and given the name, 'OVPEARLS07'.

Asexual Reproduction: Asexual reproduction of the new cultivar 'OVPEARLS07', by way of rooting leaf cuttings, was first initiated in March of 2009 at the inventor's commercial greenhouse in Bleiswijk, the Netherlands. Through eight subsequent generations, the unique features of this cultivar have proven to be stable and true to type.

SUMMARY OF THE INVENTION

The cultivar 'OVPEARLS07' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS07'. These characteristics in combination distinguish 'OVPEARLS07' as a new and distinct *Echeveria* cultivar:

1. 'OVPEARLS07' exhibits a globular plant form with an abundance narrow succulent foliage that is tightly held in a basal rosette; and
2. 'OVPEARLS07' exhibits greyed-green foliage that is lightly to moderately covered with lighter greyed-green epicuticular wax; and
3. 'OVPEARLS07' exhibits foliage that is margined dark red at and near the apex.

BOTANICAL DESCRIPTION OF THE PLANT

Figure 1:
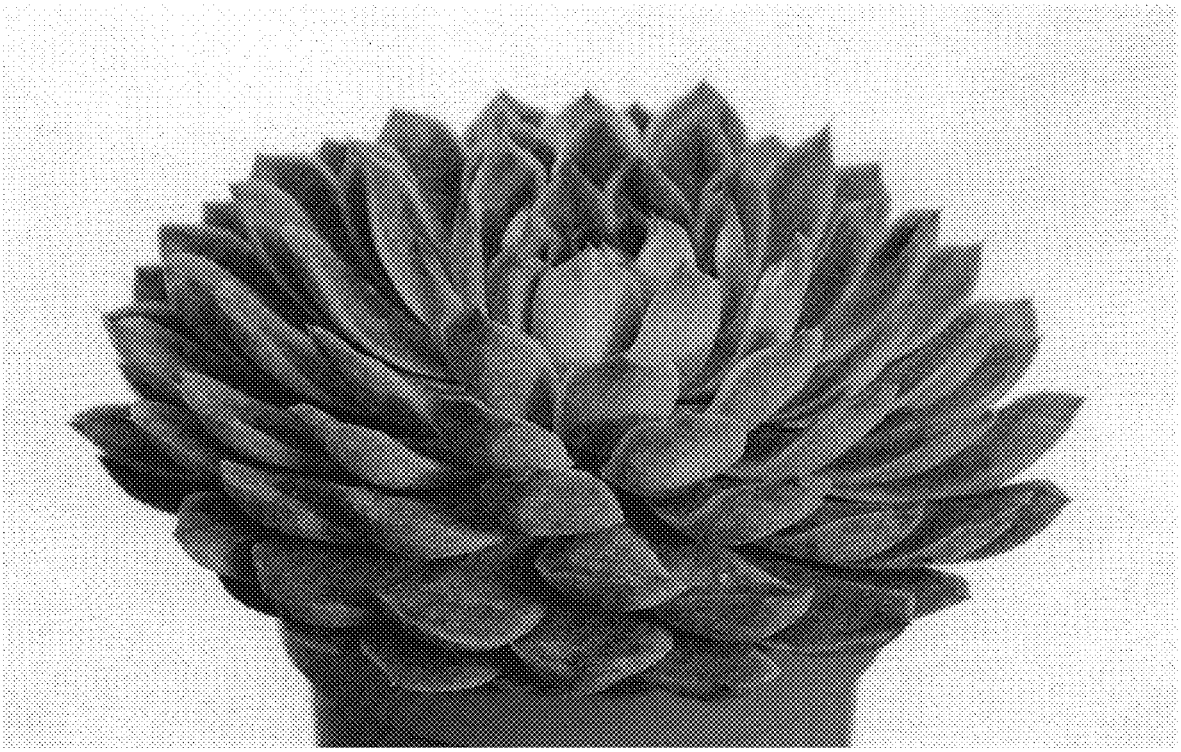
FIG. 1 illustrates, as nearly true as it is reasonably possible to make the same in color photographs of this type, an exemplary plant of 'OVPEARLS07' grown in a commercial greenhouse in Bleiswijk, the Netherlands. This plant is approximately 1 year old, shown planted in a 12 cm container.
Figure 2:
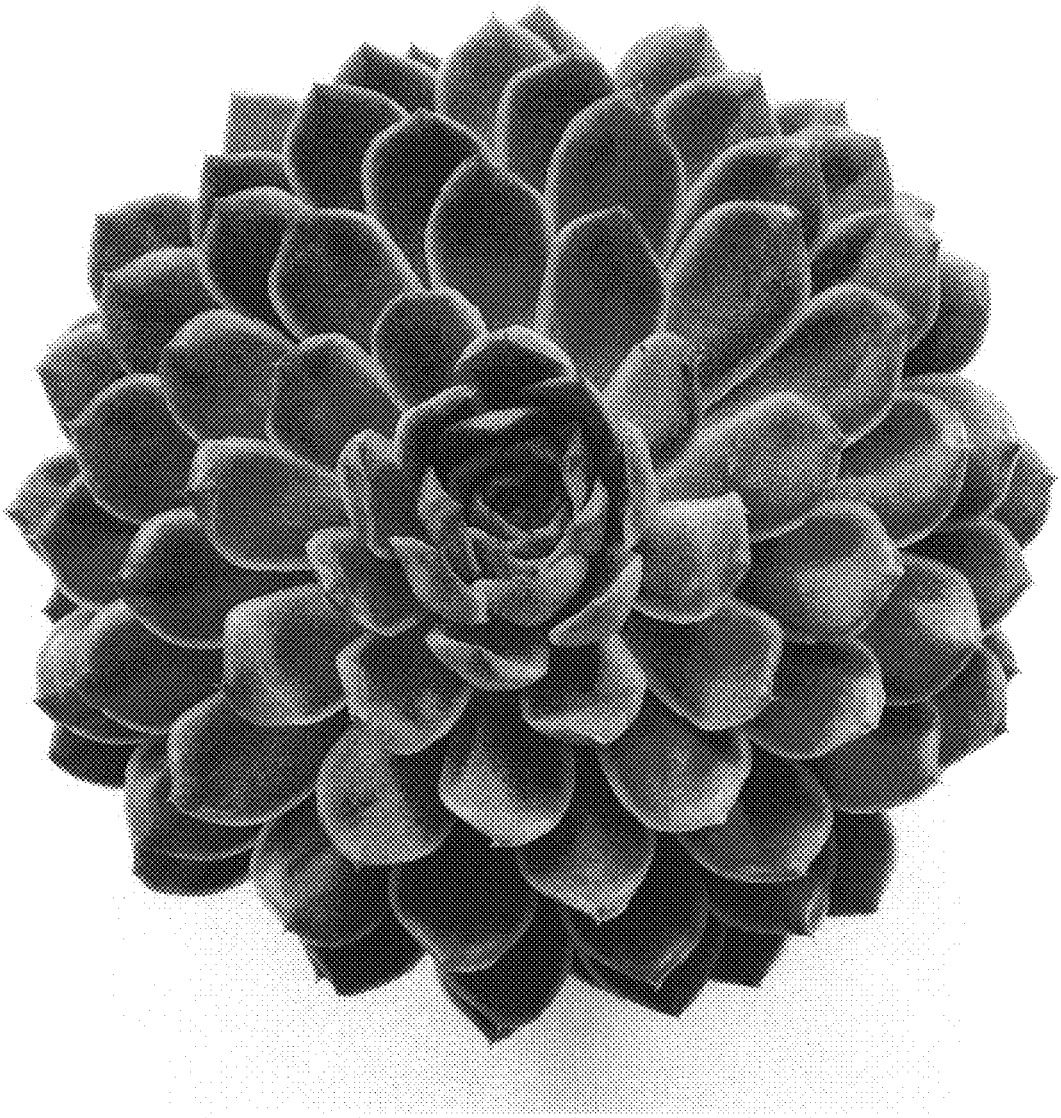
FIG. 2 illustrates, as nearly true as it is reasonably possible to make the same in color photographs of this type, the typical foliage arrangement of 'OVPEARLS07'.
Figure 3:
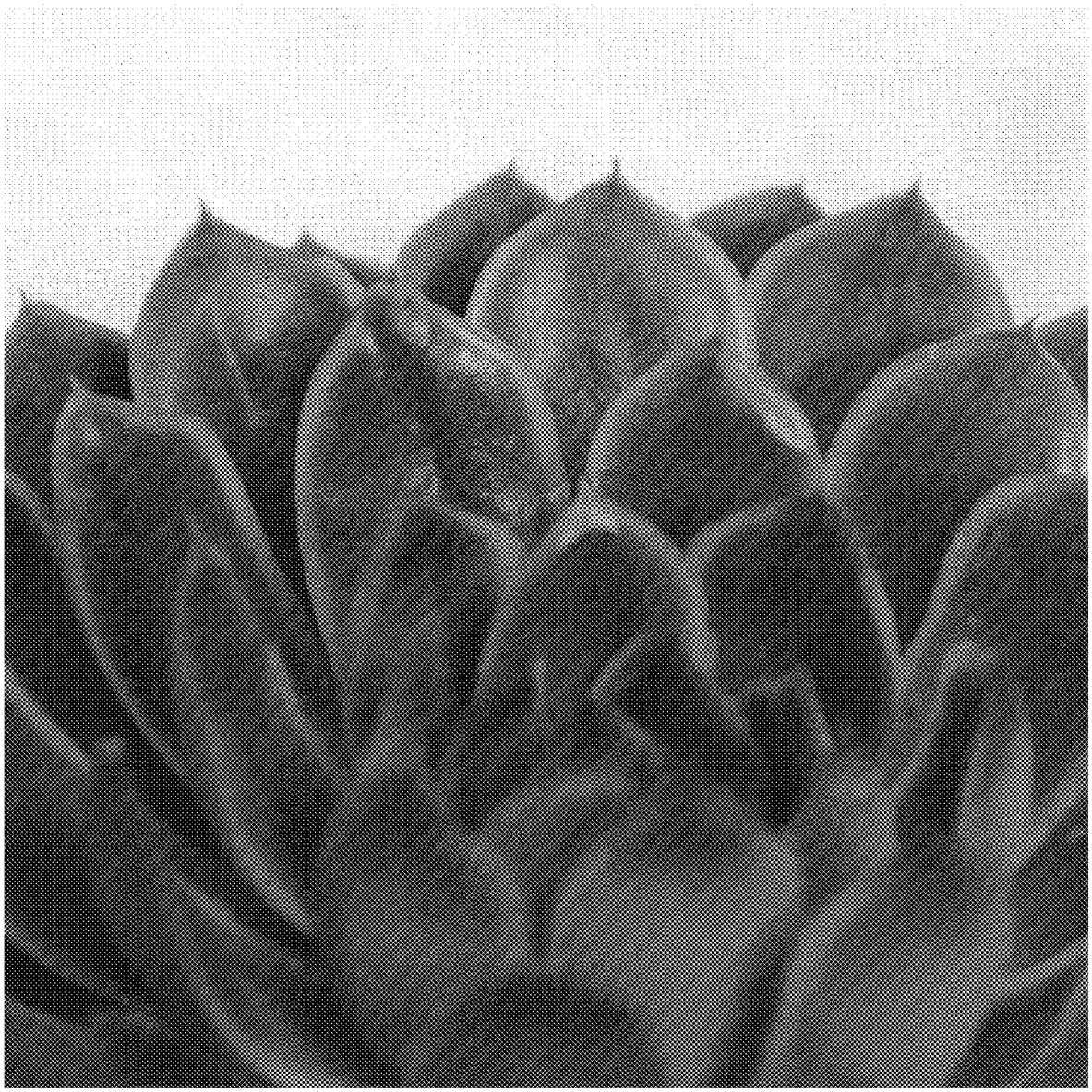
FIG. 3 illustrates, as nearly true as it is reasonably possible to make the same in color photographs of this type, the adaxial surface of the mature foliage 'OVPEARLS07'.
Figure 4:
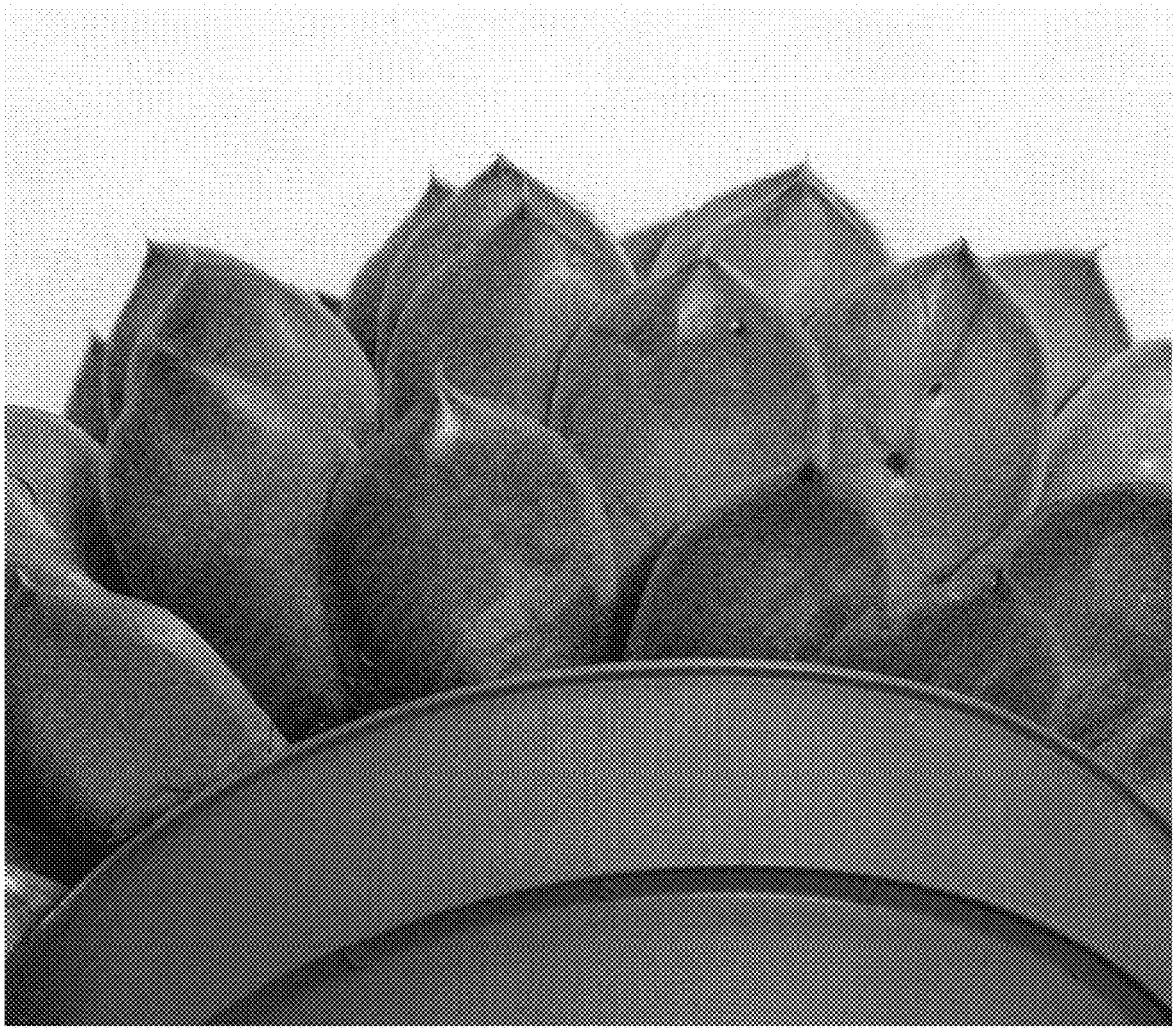
FIG. 4 illustrates, as nearly true as it is reasonably possible to make the same in color photographs of this type, the abaxial surface of the mature foliage 'OVPEARLS07'.

The following observations and measurements made in November of 2019 describe averages from a sample set of six specimens of 1 year old 'OVPEARLS07' plants grown in 12 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS07' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS07' and a comparison with the parents and closest known comparator is provided below.

Plant description:

*Growth habit*.—Succulent perennial with foliage growing in a compact, non-branched basal rosette.

*Plant form*.—Globular.

*Height from soil level to top of foliar plane*.—7.8 cm.

*Plant spread*.—Average of 18.4 cm.

*Growth rate*.—Moderately fast.

*Plant vigor*.—Moderately to highly vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Rosette.

*Division*.—Simple.

*Attachment*.—Sessile.

*Quantity*.—Approximately 148 leaves per rosette.

*Shape*.—Narrow obovate to broad oblanceolate.

*Dimensions*.—8.4 cm long, 2.7 cm wide, and 0.8 cm thick.

*Aspect*.—Slightly concave and curled upward.

*Attitude*.—Foliage is tightly held upright at and near the center of the rosette and becomes progressively more relaxed towards the outer whorls of foliage.

*Apex*.—Bluntly apiculate.

*Base*.—Long cuneate.

*Margin*.—Entire; not undulated.

*Pubescence, texture and luster of the adaxial surface*.—Glabrous, smooth, and lightly to moderately glaucescent.

*Pubescence, texture and luster of the abaxial surface*.—Glabrous, smooth, and lightly to moderately glaucescent.

*Color*.—Juvenile foliage, adaxial surface — Greyed-green, nearest to RHS 189A, and fading to in between yellow-green and greyed-green towards the base, nearest to RHS 145B and 193A; margined greyed-green, nearest to a mixture of RHS 190C and 190D, and becoming greyed-purple at the apex, nearest to RHS 185C. Leaves are covered with a thin layer of epicuticular wax which is colored greyed-green, nearest to a mixture of RHS 188B and 188C. Juvenile foliage, abaxial surface — Greyed-green, nearest to a mixture of RHS 189A and 189B, and fading lighter towards the base, nearest to a mixture of RHS 192C and 192D; margined greyed-green, nearest to a mixture of RHS 190C and 190D, and becoming greyed-purple at the apex, nearest to RHS 185C. Leaves are covered with a thin layer of epicuticular wax which is colored greyed-green, nearest to a mixture of RHS 188B and 188C. Mature foliage, adaxial surface — Greyed-green, nearest to in between RHS 189A and 191A, and fading to in between yellow-green and greyed-green towards the base, nearest to RHS 145B and 193A; margined greyed-green, nearest to a mixture of RHS 190C and 190D, and becoming greyed-purple at the apex, nearest to RHS 185C. Leaves are covered with a thin layer of epicuticular wax which is colored greyed-green, nearest to a mixture of RHS 188B and 188C. Mature foliage, abaxial surface — Greyed-green, nearest to a mixture of RHS 191A and 191B, and fading to in between yellow-green and greyed-green towards the base, nearest to RHS 147D and 193A; margined greyed-green, nearest to a mixture of RHS 192B and 192C, and becoming greyed-purple towards and at the apex, nearest to RHS 185B. Leaves are covered with a thin layer of epicuticular wax which is colored greyed-green, nearest to a mixture of RHS 188B and 188C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANTS

Plants of the new cultivar 'OVPEARLS07' differ from the seed parent, an unnamed *Echeveria agavoides* plant (not patented) in the following characteristics described in Table 1 below.

TABLE 1

| Characteristic | 'OVPEARLS07' | The seed parent. |
|---|---|---|
| General coloration of the foliage. | Darker greyed-green. | Lighter greyed-green. |
| General coloration of the foliage margins along the proximal portion. | Light greyed-green, generally appearing as a dull white coloration. | Light greyed-green, general appearing as a brighter white coloration by comparison to 'OVPEARLS07'. |
| General coloration of the foliage margins towards and at the apex. | Greyed-purple, generally appearing as a dark red coloration. | No red coloration. |

Plants of the new cultivar 'OVPEARLS07' differ from the pollen parent, an unnamed *Echeveria elegans* var. *simulans* plant (not patented) in the following characteristics described in Table 2 below.

TABLE 2

| Characteristic | 'OVPEARLS07' | The pollen parent. |
|---|---|---|
| General coloration of the foliage. | Darker greyed-green. | Lighter greyed-green. |
| General coloration of the foliage margins along the proximal portion. | Light greyed-green, generally appearing as a dull white coloration. | Light greyed-green, general appearing as a brighter white coloration by comparison to 'OVPEARLS07'. |

TABLE 2-continued

| Characteristic | 'OVPEARLS07' | The pollen parent. |
|---|---|---|
| General coloration of the foliage margins towards and at the apex. | Greyed-purple, generally appearing as a dark red coloration. | No red coloration. |

COMPARISONS WITH THE CLOSEST KNOWN COMPARATOR

Plants of the new cultivar 'OVPEARLS07' differ from the most similar variety known to the inventor, *Echeveria* 'OVPEARLS05' (U.S. patent application Ser. No. 16/899,822), in the following characteristics described in Table 3 below.

TABLE 3

| Characteristic | 'OVPEARLS07' | 'OVPEARLS05' |
|---|---|---|
| Abundance of foliage. | More abundant. | Less abundant. |
| General coloration of the foliage. | Greyed-green but generally appearing as closer to green by comparison to 'OVPEARLS05'. | Greyed-green but generally appearing as closer to grey by comparison to OVPEARLS07'. |
| General coloration of the foliage margins at and towards the apex. | Less greyed-purple coloration. | More greyed-purple coloration. |

That which is claimed is:

1. A new and distinct variety of *Echeveria* plant named 'OVPEARLS07', substantially as described and illustrated herein.

* * * * *